United States Patent [19]

Shalaby et al.

[11] 4,208,511

[45] Jun. 17, 1980

[54] ISOMORPHIC COPOLYOXALATES AND SUTURES THEREOF

[75] Inventors: Shalaby W. Shalaby, Lebanon; Dennis D. Jamiolkowski, Long Valley, both of N.J.

[73] Assignee: Ethicon, Inc., Somerville, N.J.

[21] Appl. No.: 915,500

[22] Filed: Jun. 14, 1978

Related U.S. Application Data

[63] Continuation-in-part of Ser. No. 752,374, Jan. 19, 1977.

[51] Int. Cl.$^2$ .............................................. C08G 63/18
[52] U.S. Cl. .......................................... 528/272; 3/1; 3/1.4; 3/1.5; 128/92 B; 128/92 C; 128/334 R; 128/335.5
[58] Field of Search .......................................... 528/272

[56] References Cited

U.S. PATENT DOCUMENTS 4,032,993   7/1977   Coquard et al. ...................... 528/272

*Primary Examiner*—Lucille M. Phynes
*Attorney, Agent, or Firm*—Wayne R. Eberhardt

[57] ABSTRACT

Synthetic absorbable sutures are prepared from copolyoxalate polymers having isomorphic sequences. The polymers are derived from mixtures of cyclic and linear diols, each having the same carbon chain length of 6 or 8 atoms. The cyclic diol may be aliphatic or aromatic. The diols are polymerized with dialkyl oxalate, preferably in the presence of an inorganic or organometallic catalyst, to obtain a highly crystalline isomorphic copolyoxalate polymer which is melt extruded and drawn to form oriented filaments. The filaments are characterized by good initial tensile and knot strength and a high order of softness and flexibility. When implanted in living animal tissue, the fibers have good strength retention over a period of at least 21 days and eventually absorb with a minimal degree of adverse tissue reaction.

8 Claims, No Drawings

ISOMORPHIC COPOLYOXALATES AND SUTURES THEREOF

CROSS REFERENCE TO RELATED APPLICATIONS

This is a continuation-in-part of application Ser. No. 752,374, filed Jan. 19, 1977.

BACKGROUND OF THE INVENTION

1. Field of the Invention

This invention relates to synthetic absorbable sutures, and more particularly, to synthetic absorbable sutures comprising extruded and oriented filaments of copolymers of polyoxalates having isomorphic sequences.

2. Description of Prior Art

Absorbable suture materials have traditionally been natural collagenous materials obtained from sheep or beef intestine, commonly known as catgut. More recently, it has been proposed to manufacture synthetic absorbable sutures from polyesters of hydroxycarboxylic acids, notably polylactide, polyglycolide, and copolymers of lactide and glycolide. Such synthetic absorbable sutures are described in U.S. Pat. Nos. 3,636,956 3,297,033 and elsewhere in the literature. Polyesters of succinic acid have also been suggested for at least partially bioresorbable surgical articles as disclosed for example in U.S. Pat. No. 3,883,901.

Among the requirements of an ideal absorbable suture are that it should have good handling properties, should approximate and hold tissue for proper healing with minimal tearing and tissue damage, should have adequate straight tensile and knot strength, should be controllably uniform in properties including dimensional stability within the body, should be sterilizable, should be absorbable by living tissue, preferably at a constant rate regardless of the place in the body or the condition of the patient and without causing such unfavorable tissue reactions as walling off, granuloma formation or excessive edema, and finally should be capable of being properly and easily tied into surgical knots.

While multifilament sutures manufactured from polymers of lactide and glycolide fulfill the above requirements to a large degree, monofilament sutures of these materials are considerably less flexible than catgut and these synthetic sutures are accordingly generally limited to a multifilament, braided construction. Sutures of glycolide polymers are also not suitable for sterilization by radiation without suffering severe degradation of physical properties.

We have discovered that copolyoxalate copolymers having isomorphic sequences can be melt extruded into pliable, monofilament fibers which have good in vivo strength retention and are absorbed in animal tissue without significant adverse tissue reaction. The fibers have good tensile and knot strength, and can be sterilized by gamma radiation without serious loss of these properties. In addition, monofilament sutures of the polymers of the present invention have a high degree of softness and flexibility not found in many synthetic absorbable sutures of the prior art.

The preparation of polyoxalate polymers is described in the art. Carothers et al, J. Amer. Chem. Soc. 52, 3292 (1930) for example, describes the ester interchange reaction of diols such as ethylene glycol, 1,3-propanediol, or 1,4-butanediol with diethyl oxalate to yield a mixture of monomer, soluble polymer and insoluble polymer. The reaction of oxalic acid and an alkylene glycol to form polyester resins is described in U.S. Pat. No. 2,111,762, while the preparation of polyesters of fiber-forming quality from dicarboxylic acids and diols is described in U.S. Pat. No. 2,071,250-1 and 2,952,652. Isomorphic polymers including polyester copolymers have been discussed in the literature[1]. The particular isomorphic copolyoxalates of the present invention however, have not previously been known, nor has their preparation or use as synthetic absorbable sutures been suggested heretofore.

[1] Isomorphism in Synthetic Macromolecular Systems, G. Allegra and I. W. Bassi, Adv. Polymer Sci. 6, 549 (1969)

It is accordingly an object of the present invention to provide new and useful polymers of isomorphic copolyoxalates and articles made therefrom. A further object of this invention is to provide synthetic absorbable sutures of isomorphic copolyoxalates. It is a yet further object of this invention to provide surgical aids and prostheses fabricated of fibers or cast or machined from blocks of isomorphic copolyoxalate polymers.

SUMMARY

Highly crystalline isomorphic polyoxalate polymers are prepared by reacting mixtures of cyclic and linear diols with dialkyl oxalate, preferably in the presence of an inorganic or organometallic catalyst. The diols comprising the reaction mixture have the same carbon chain length separation between terminal OH groups of 6 or 8 carbon atoms. The cyclic diol may be trans 1,4-cyclohexane dialkanol or p-phenylene dialkanol and comprises from about 5 to 95 mol percent, and preferably from 40 to 75 mol percent of the total diol reactant.

Copolymers prepared by the transesterification reaction of the two diols and diethyl oxalate are melt extruded into highly crystalline filaments suitable for use as synthetic absorbable sutures. Drawn and oriented filaments are characterized by high tensile and knot strength, a Young's modulus in most cases of less than about 600,000 psi providing a high order of filament softness and flexibility, and good strength retention and minimal tissue reaction in vivo.

DESCRIPTION OF PREFERRED EMBODIMENTS

Polymers of the present invention are comprised of isomorphic units of cyclic and linear oxalates and have the general formula $$\left[-O-R-O-\underset{\underset{O}{\|}}{C}-\underset{\underset{O}{\|}}{C}-\right]_x$$

wherein each R is

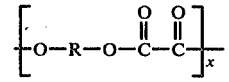   I or

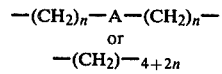   II with from about 5 to 95 mol percent, and preferably from about 40 to 75 mol percent of R groups being I; A is trans 1,4-cyclohexylene or p-phenylene, n is 1 or 2 and is the same for I and II, and x is the degree of polymerization resulting in a polymer having an inherent viscosity of at least 0.3 as determined on a solution of 1 gm of polymer in 1 liter of chloroform or hexafluoroisopropanol at 25° C. Most preferably, the inherent viscosity of the polymer is at least about 0.5 and the polymer is fiber forming.

Polymers of the present invention are conveniently prepared by an ester interchange reaction between the aforedescribed mixture of diols and a lower ester of oxalic acid, preferably in the presence of an ester interchange catalyst. The preferred ester of oxalic acid is diethyl oxalate. The ester interchange is most preferably conducted in two stages wherein the reactants are first heated with stirring under a nitrogen atmosphere to form a prepolymer with the removal of ethanol, followed by postpolymerization under heat and reduced pressure to obtain a final polymer of the desired molecular weight and fiber forming quality. Polymers with low or moderate degrees of polymerization are postpolymerized in the liquid state or as finely-divided solid particles, depending on their melting temperature range.

The polymer is melt extruded through a spinnerette in a conventional manner to form one or more filaments which are subsequently drawn about 4× to 6× in order to achieve molecular orientation and improve tensile properties. The resulting oriented filaments have good tensile and dry knot strength and good in vivo strength retention.

It is well documented that the crystallinity and hence suitability for fiber-formation in both the AB and AA-BB type polyesters decreases significantly when the mol fraction of the major comonomer sequence decreases below about 80%. In some instances, if the comonomer sequences are isomorphic, chains composed of slightly less than 80% of the major sequences can pack into a crystalline form. However, randomly constructed copolyester chains based on almost equal amounts of the isomorphic comonomer sequences are generally found to be non-crystalline and poor fiber formers. Contrary to this general rule, the isomorphic copolyesters of the present invention display an unexpectedly high level of crystallinity of about 45% in a 50/50 copolyester. The polymers of the present invention are also unusual in that all copolymers through the entire composition range of from 5 to 95% of each isomorphic comonomer demonstrate levels of crystallinity comparable to those encountered in the parent homopolymers; namely between 30 and 50% depending on the thermal history. A similarly striking observation characteristic of these copolyesters is their display of melting endotherms, as shown by DSC, for the crystalline regions of all copolymers within the composition range of from about 5 and 95 mol % of each isomorphic comonomer. Constructed curves of the melting temperature versus composition did not reveal any positive eutectic composition in these systems. The X-ray and DSC data suggest strongly the uncommon presence of almost complete isomorphism in the copolyesters of the present invention.

Dimensional stability and tensile strength retention of the oriented filaments may be enhanced by subjecting the filaments to an annealing treatment. This optional treatment consists of heating the drawn filaments to a temperature of from about 40° to 130° C., most preferably from about 60° to 110° C. while restraining the filaments to prevent any substantial shrinkage. The filaments are held at the annealing temperature for a few seconds to several days or longer depending on the temperature and processing conditions. In general, annealing at 60° to 110° C. for up to about 24 hours is satisfactory for the polymers of the present invention. Optimum annealing time and temperature for maximum fiber in vivo strength retention and dimensional stability is readily determined by simple experimentation for each fiber composition.

Filaments of the present invention may be used as sutures in either a monofilament or a multifilament construction. Multifilament sutures are preferably braided but may also be twisted or covered in accordance with common practice. For use as sutures, it is necessary that the fibers be sterile, and sterilization may be accomplished by exposing the fibers to Cobalt 60 gamma radiation or to ethylene oxide. Such sterilization technique are well known and commonly practiced in suture manufacture.

Since the function of a suture is to join and hold severed tissue until healing is well along, and to prevent wound separation as a result of movement of exercise, a suture must meet certain minimum standards of strength. It is particularly important that strength be maintained when knots are tied and during the actual procedure of drawing tight a suitable knot. Sutures prepared from oriented filaments of the present invention are characterized by a straight tensile strength of at least about 30,000 psi and a knot strength of at least about 20,000 psi, although significantly higher strengths may be obtained.

The preparation of high molecular weight oriented filaments of isomorphic polyoxalates is further illustrated by the following examples where all percentages are on a molar basis unless otherwise noted. The following analytical methods were used to obtain the data reported in the examples. Inherent viscosity ($\eta_{inh}$) was obtained on polymer solutions (1 gram/liter) in chloroform or hexafluoro-isopropanol (HFIP) at 25° C. The infrared spectra of polymer films (cast from $CHCl_3$ or HFIP) were recorded on a Beckman Acculab 1 spectrophotometer. The NMR spectra of the polymer solutions in $CDCl_3$ were recorded on an MH-100 or CFT-20 spectrophotometer. A DuPont 990 DSC apparatus were used to record the glass transition ($T_g$), crystallization ($T_c$) and melting ($T_m$) temperatures of the polymers under nitrogen, using about 5 mg samples and a heating rate of 10° C./min or as otherwise specified. The thermogravimetric analysis (TGA) data of the polymers were recorded under nitrogen using a DuPont 950 TGA apparatus and a heating rate of 10° or 20° C./min with about 10 mg samples. A Phillips vertical goniometer with graphite crystal monochromatized copper $K_\alpha$ radiation was used to obtain the X-ray powder and fiber diffraction patterns of the polymers. Crystallinity was determined by the method of Hermans and Weidinger and the diffractometer patterns were resolved with a DuPont 310 curve analyzer.

In vitro hydrolysis of polymer discs (about 1.2 g, 2.2 cm diameter) and monofilaments (7-25 mil) was conducted at 37° C. in phosphate buffer comprising a solution of 27.6 g sodium dihydrogenphosphate monohydrate in 1000 ml water adjusted to pH 7.25 with sodium hydroxide.

In vivo absorption (muscle) was determined by implanting two 2 cm segments of monofilament fiber into the left gluteal muscles of female Long Evans rats. The implant sites were recovered after periods of 60, 90, 120 and 180 days and examinated microscopically to determine the extent of absorption. In vivo absorption (subcutaneous) is a non-histological technique in which continuous observation of the biological degradation of segments of suture is made by implanting two segments of suture, 2 cm long, into the abdominal subcutis of young female rats. The implants are readily visible when the skin is wetted with propylene glycol and extent of absorption can be determined by subjective visual examination.

In vivo strength retention was determined by implanting segments of sutures in the posterior dorsal subcutis of female Long Evans rats for period of 5 to 30 days. The sutures were recovered at the designated periods and pull-tested for straight tensile strength.

In vitro strength retention was determined by placing segments of sutures in the afore-defined buffer at 50° C. for periods of 2 to 4 days. The sutures were recovered at the designated periods and pull-tested for straight tensile strength.

EXAMPLES

General Polymerization Procedure

Diethyl oxalate was heated with selected diols in a mechanically-stirred reactor using a stannous alkanoate or organic titanate catalyst. The reaction was conducted under a nitrogen atmosphere at suitable temperatures until a substantial portion of the calculated amount of ethanol was obtained. Postpolymerization of the resulting prepolymer was then continued under reduced pressure using a suitable heating scheme. At the end of the postpolymerization period, the molten polymer was allowed to cool slowly at room temperature, isolated, ground and dried at 25° C. to 80° C. (depending on the polymer $T_m$) in vacuo for at least one day. Alternatively, the prepolymer can be postpolymerized partially in the liquid state, cooled, and then postpolymerized further in the solid state as finely divided particles. Detailed experimental conditions for the preparation of representative samples of isomorphic polyoxalates and important properties of the resulting polymers are presented below.

EXAMPLE I

95/5 Poly (trans 1,4-Cyclohexylenedicarbinyl-co-hexamethylene Oxalate)

Distilled diethyl oxalate (19.0 g, 0.130 mol), recrystallized trans 1,4-cyclohexanedimethanol (19.8 g, 0.137 mol), 1,6-hexadiol (0.856 g, 0.00724 mol) and stannous octoate (0.33 M in toluene; 0.080 ml, 0.026 mmol) were added under dry and oxygen-free conditions to a glass reactor equipped for magnetic stirring. The prepolymer was formed by heating the mixture at 120° C. for 3 hours under nitrogen at 1 atmosphere while allowing the formed ethanol to distill, followed by heating at 160° C. for 2 hours. The prepolymer was then heated in vacuo (0.05 mm Hg) at 220° C. for 1 hour, and the postpolymerization completed by heating at 215° C. for an additional 6 hours. The polymer was then allowed to cool to room temperature, isolated and ground, and finally dried in vacuo at room temperature.

Polymer Characterization: $\eta$inh in $CHCl_3=0.05$. DSC (20° C./min.): $T_m=210°$ C.

Polymer Melt-Spinning: The polymer was spun using an Instron Rheometer with a 30 mil die at 207° C.

In Vitro Evaluation: The undrawn fibers lost 21 and 66 percent of their initial mass after immersion in phosphate buffer at 37° C. for 42 and 127 days, respectively.

EXAMPLE II

85/15 Poly (1,4-Cyclohexylenedicarbinyl-co-hexamethylene Oxalate)

Distilled diethyl oxalate (58.4 g, 0.400 mols), recrystallized trans 1,4-cyclohexanedimethanol (less than 1% cis isomer; 53.9 g, 0.374 mols), 1,6-hexanediol (7.8 g, 0.066 mol), and stannous octoate (0.33 M in toluene; 0.40 ml, 0.13 mmol) were added under dry and oxygen-free conditions to a glass reactor equipped for mechanical stirring. The mixture was heated at 120° and 150° C. for 2 and 3 hours, respectively, under nitrogen at one atmosphere while the formed ethanol distilled. The prepolymer was allowed to cool, then reheated to 200° C. under reduced pressure (0.1 mm Hg). Temperatures of 200°, 220° and 230° C. were maintained for 2, 3 and 4 hours while the collection of distillates continued. The resulting polymer ($\eta$inh in $CHCl_3=0.49$) was cooled, isolated, ground (2 mm screen size), and then dried in vacuo at room temperature. Portions (30 g) of this ground polymer were postpolymerized in the solid state in glass reactors equipped for magnetic stirring by heating in vacuo (0.1 mm Hg) at 185° C. for 22 hours.

Polymer-Characteristization: $\eta$inh in $CHCl_3=1.14$. DSC (20° C./min.): $T_m=187°$ C.

Polymer Melt-Spinning: The polymer was spun at 230° C. using an Instron Rheometer with a 40 mil die. The fiber was quenched in ice water, wound, dried and subsequently drawn.

Fiber Properties: Fibers drawn 5X in two stages, 4X at 62° C. followed by 1.25X at 119° C. exhibited the following properties: diameter=8.5 mils, straight tensile strength=$8.39 \times 10^4$ psi; knot tensile strength=$5.06 \times 10^4$ psi; modulus=$6.61 \times 10^5$ psi; elongation=15%.

In Vivo Evaluation: Sterilized (via $\gamma$-radiation, 2.5 Mrads), drawn monofilament (8.5 mils) retained 89, 75, 10 and zero percent of its initial breaking strength (4.8 lbs.) after subcutaneous implantation in rat muscle for 3, 7, 14 and 21 days respectively. Drawn filaments implanted into the gluteal muscles of rats elicited median tissue responses in the slight range throughout a 180 day post-implanation period. Filaments drawn 4X at 60° C. followed by 1.25X at 110° C. and having a straight tensile of $6.76 \times 10^4$ psi showed indications of initial degradation 20 to 26 weeks after implantation.

In Vitro Evaluation: Fibers drawn 4X at 60° C. (exhibiting a straight tensile of $4.33 \times 10^4$ psi) lost 40 percent of their initial mass after immersion in phosphate buffer at 37° C. for 84 days.

EXAMPLE III

80/20 Poly (1,4-Cyclohexylenedicarbinyl-cohexamethylene Oxalate)

Distilled diethyl oxalate (43.8 g, 0.300 mol), recrystallized trans 1,4-cyclohexanedimethanol (cis isomer content=1.0%, 36.3 g, 0.252 mol), 1.6-hexanediol (7.4 g, 0.063 mol), and stannous oxalate (12.4 mg., 0.060 mmol) were added under dry and oxygen-free conditions to a glass reactor equipped for mechanical stirring. The prepolymer was formed by heating the mixture at 120° C. for 2 hours under nitrogen at 1 atmospheere while allowing the formed ethanol to distill, followed by 160° C. for 2.5 hours. The mixture was allowed to cool, then reheated in vacuo (0.1 mm Hg) to 140° C. and maintained until the prepolymer melted. The temperature was then increased to 190° C., maintained for 30 minutes, then raised to 200° C. for 1.5 hours. The melt post-polymerization of the stirred polymer was completed by heating at 220° C. for 4.5 hours. The polymer was cooled, isolated, ground (screen size=2 mm) and dried in vacuo at room temperature. To obtain the final product, the ground polymer was post-polymerized in the solid state in a glass reactor equipped for magnetic stirring by heating at 180° C. in vacuo (0.05 mm Hg) for 24 hours while allowing the formed diols to distill.

Polymer Characterization: $\eta$inh in $CHCl_3 = 1.33$. DSC (20° C./min.): $T_m = 205$° C.

Polymer Melt-Spinning: The polymer was spun at 240° C. using an Instron Rheometer equipped with a 40 mil die. The extruded filaments were quenched in ice water, wound, then dried at room temperature in vacuo, and subsequently drawn 4×.

Fiber Properties: Diameter=9.0 mils; straight tensile strength=$7.31 \times 10^4$ psi; knot tensile strength=$3.46 \times 10^4$ psi; modulus=$7.7 \times 10^5$ psi; elongation=15%.

In Vivo Evaluation: Sterilized (by $\gamma$-radiation, 2.5 Mrads), fibers (9.0 mil) retained 85, 20 and zero percent of their initial breaking strength (4.2 lbs.) after subcutaneous implantation in rat muscles for 3, 7 and 14 days, respectively. These fibers were also implanted into the gluteal muscles of rats to determine tissue response and absorption characteristics. The median tissue response elicited by the samples was in the slight range after 5 days post implantation and in the minimal range after 42 days; absorption of the samples was first noted at 120 days and by 180 days approximately fifty percent of the material had been absorbed.

EXAMPLE IV

80/20 Poly (1,4-Cyclohexylenedicarbinyl-cohexamethylene Oxalate)

Distilled diethyl oxalate (23.4 g, 0.160 mol), recrystallized trans 1,4-cyclohexanedimethanol (cis isomer content=6.3%; 20.0 g, 0.139 mol), 1,6-hexanediol (4.1 g, 0.035 mol) and Tyzor OG* (0.117 M in toluene, 0.28 ml, 0.033 mmols) were added under dry and oxygen-free conditions to a glass reactor equipped for magnetic stirring. A prepolymer was formed by heating the mixture at 120° C. for 19 hours under nitrogen at 1 atmosphere while allowing the formed ethanol to distill. The pressure was then reduced (0.05 mm Hg) and heating at 120° C. continued for 30 minutes longer. The temperature was then increased and maintained at 180° C., 190° C. and 200° C. for 2, 5 and 2 hours, respectively, while removing excess and formed diols. The polymer was allowed to cool, isolated, ground, and dried in vacuo at room temperature.
*Tyzor OG, a titanium glycolate catalyst manufactured by E. I. DuPont de Nemours and Co., Wilmington, Del., 19898

Polymer Characterization: $\eta$inh in $CHCl_3=0.46$. DSC (10° C./min.): $T_m=171$° C. TGA (10° C./min. under $N_2$): 0.25% weight lost at 275° C.

Polymer Melt-Spinning: The polymer was spun using an Instron Rheometer with a 30 mil die at 172° C. The extruded filaments were quenched in ice water, dried in vacuo at room temperature, and finally drawn 5× at 43° C.

Fiber Properties: $\eta$inh in $CHCl_3=0.42$.

X-ray: Major reflections correspond to 8.9 (W), 4.84 (M), 4.41 (S) and 3.42 Å (W) d-spacings; 26% crystallinity. (Undrawn filaments were found to be 22% crystalline which increased to 31% by annealing at 70° C. for one hour).

Physical Properties: Diameter=11.1 mils; straight tensile strength=$2.07 \times 10^4$ psi; elongation=35%.

In Vivo Evaluation: The rate of absorption and tissue response of drawn filaments was determined by implantation into the ventral abdominal subcutis of Long-Evans rats. Some evidence of filament degradation was noted 11 to 14 weeks after implantation, with the bulk of the fiber being absorbed by 20 to 23 weeks. No tissue reaction to the implants was noted at any period.

In Vitro Evaluation: The drawn fibers exhibited a 43% decrease in mass after immersion in the phosphate buffer at 37° C. for 28 days.

EXAMPLE V

67/33 Poly(trans 1,4-cyclohexylenedicarbinyl-cohexamethylene Oxalate)

Distilled diethyl oxalate (40.0 g, 0.274 mol), recrystallized trans 1,4-cyclohexanedimethanol (25.9 g, 0.180 mol), 1,6-hexanediol (10.6 g, 0.0897 mol), and stannous octoate (0.33 M in toluene; 0.16 ml. 0.053 mmol) was added to a glass reactor equipped for mechanical stirring. The prepolymer was formed by heating the mixture under nitrogen at 120° C. for 9 hours, followed by 125° C. for 9 hours while collecting the distillates. The prepolymer was cooled, then reheated in vacuo (0.03 mm Hg) and maintained at 80, 120, 150, 170 and 180° C. for 1, 2, 2, 3 and 1.5 hours, respectively. The postpolymerization of the polymer melt was completed by heating at 195° C. for 6 hours while continuing to stir and remove distillates. The polymer was cooled, isolated, ground, and then dried at room temperature.

Polymer Characterization: $\eta$inh in $CHCl_3=0.49$. DSC (20° C./min.): $T_m=179$° C.

Polymer Melt Spinning: The polymer was spun at 175° C. using an Instron Rheometer with a 30 mil die. The resulting fibers were subsequently drawn 41× at 50° C.

Fiber Properties: Diameter=9.3 mils, straight tensile stength=$2.65 \times 10^4$ psi, knot tensile strength=$2.21 \times 10^4$ psi, modulus=$3.7 \times 10^5$ psi.

In Vivo Evaluation, Tissue Reaction: Two centimeter long samples of sterilized (by $\gamma$-radiation, 2.5 Mrads) drawn fiber were implanted subcutaneously in the abdominal wall of young female Long Evans strain rats. At intervals of 3, 14, 28, 56 and 90 days, two rats were sacrificed for examination of implants. The skin containing the fibers was excised and affixed to plastic sheets for preservation in formalin. Two tissue blocks were cut transversely from each site and embedded in paraffin for histologic preparation. Eight strained samples were examined at each interval for tissue reaction to the fibers. Only mild foreign body reactions were detected.

In Vivo Evaluation, Absorption: Fiber segments sterilized by $\gamma$-radiation (2.5 Mrads) approximately 2 cm in length were inserted into the ventral abdominal subcutis of Long Evans rats (100 g, female) to determine the rate of absorption of the drawn fibers. One to two rats were sacrified after various periods after implantation. The skin containing the implant sites was removed and dried. These preparations were examined and evaluated using both dissecting and transmission microscopes. Estimates of the amount of implant remaining were based on the length of the segment or fragments remaining and the decrease in the surface area made by palpating the implant in the dried hide and comparing it with a one week old preparation. Implants were fragmented at one week; migration and clumping of fragments was noted at subsequent kill periods. Evidence of degradation was first seen 16 weeks after implantation. Palpable fragments, in diminishing amounts, were present until 30 weeks. Quantitatively, about 100, 75, 45, 40, 20, 15 and 5 or less percent of the suture remained after 14, 16, 20, 23, 26, 30 and 36 weeks.

EXAMPLE VI

50/50 Poly (trans 1,4-cyclohexyldicarbinyl-cohexamethylene Oxalate

Distilled diethyl oxalate (38.0 g, 0.260 mol), recrystallized trans 1,4-cyclohexanedimethanol (20.2 g, 0.140 mol), 1,6-hexanediol (16.5 g, 0.140 mol), and stannous octoate (0.33 M in toluene, 0.16 ml, 0.053 mmol) were added under dry and oxygen-free conditions to a mechanically stirred glass reactor. Under nitrogen at one atmosphere, the mixture was heated to and maintained at 120° C. for 20 hours, while allowing the formed ethanol to distill. The prepolymer was cooled and then reheated in vacuo (0.05 mm Hg) to and maintained at 80°, 120°, 140°, 165°, 175°, 185°, and 195° C. for 1, 1, 3, 3.5, 2, 1 and 1 hour respectively. The removal of the diols was continued by heating at 200° C. for 8 hours to complete the postpolymerization. The polymer was cooled, isolated, ground, and then dried in vacuo at room temperature.

Polymer Characterization: $\eta$inh in $CHCl_3$ = 0.36. DSC (20° C./min.): $T_m$ = 138° C.

Polymer Melt Spinning: The polymer was spun at 136° C. using an Instron Rheometer (40 mil die) and was immediately drawn 5× at 53° C.

Fiber Properties:

X-ray Data: Major reflections correspond to 8.9 (W), 4.84 (M), 4.41 (S), and 5.40 Å (W) d-spacings; 36% crystallinity.

Physical Properties: Diameter = 10.6 mils, straight tensile strength = $1.36 \times 10^4$ psi, knot tensile strength = $1.13 \times 10^4$ psi, modulus = $1.33 \times 10^5$ psi, elongation = 27%.

In Vivo Evaluation: Sterilized (by $\gamma$-radiation) drawn fiber segments (2 centimeters in length) were implanted into the ventral abdominal subcutis for study of the rate of absorption and tissue reaction.

At one week the implants were fragmented, clumping, and migrating, with the bulk of the suture being absorbed between 6 to 11 weeks. Thereafter, fragments with scattered birefringent particles or birefringent particles in a shelllike outline were observed. The birefringent particles decreased in amount until at 36 weeks only a few widely scattered particles were noted.

Only mild foreign body reactions were observed to be elicited by the sterilized drawn fiber segments during the test intervals of 3, 14, 28, 48, 90 and 180 day post implantation.

In Vitro Evaluation: Undrawn fibers exhibited a 57 percent decrease in their initial mass after immersion in phosphate buffer at 37° C. for 28 days.

EXAMPLE VII

50/50 Poly (trans 1,4-cyclohexyldicarbinyl-cohexamethylene Oxalate)

Distilled diethyl oxalate (58.5 g, 0.400 mol), recrystallized trans 1,4-cyclohexanedimethanol (cis isomer content = 0.7%; 29.7 g, 0.206 mol), 1,6-hexanediol (24.3 g, 0.206 mol), and stannous oxalate (16.5 mg, 0.080 mmols), were added under dry and oxygen-free conditions to a mechanically stirred glass reactor. The mixture was heated under nitrogen at one atmosphere to and maintained at 120° and 160° C. for 3 and 2 hours respectively while allowing the formed ethanol to distill. The prepolymer was cooled and then reheated in vacuo (0.05 mm Hg) and maintained at 170°, 190° and 205° C. for 3, 2.5 and 3 hours respectively while continuing to remove excess and formed diol to complete the postpolymerization. The polymer was cooled, isolated, ground, and then dried in vacuo at room temperature.

Polymer Characterization: $\eta$inch in HFIP = 1.07 DSC (20° C./min.) $T_m$ = 132° C.

Polymer Melt Spinning: The polymer was spun at 150° C. using an Instron Rheometer (40 mil die) and was drawn 4X at 50° C. followed by 1.5X at 72° C.

Fiber Properties:

X-ray Data: Major reflections correspond to 9.11 (MS), 4.82 (S), 4.60 (W), 4.37 (S) and 3.45 Å (W) d-spacings; 46% crystallinity.

Physical Properties: Diameter = 7.6. straight tensile strength = 51,300 psi, knot. tensile strength = 36.400 psi, elongation = 31%.

EXAMPLE VIII

30/70 Poly (trans 1,4-cyclohexylenedicarbinyl-cohexamethylene Oxalate)

Distilled diethyl oxalate (36.5 g, 0.250 mol), recrystallized trans 1,4-cyclohexanedimethanol (11.5 g, 0.0797 mol), 1,6 hexanediol (22.4 g, 0.190 mol), and stannous octoate (0.33 M in toluene; 0.16 ml, 0.053 mmol) were added under dry and oxygen-free conditions to a mechanically stirred reactor. The mixture was heated to and maintained at 125, 140 and 160° C. for 2, 2 and 1 hour, respectively, under nitrogen at one atmosphere while allowing the formed ethanol to distill. The prepolymer was cooled and then reheated in vacuo (0.1 mm Hg) and maintained at 150° and 185° C. for 16 and 3 hours, respectively. The postpolymerization was completed by maintaining the polymer at 200° C. for 5.5 hours while continuing to remove the diols under vacuum. The polymer was then cooled, isolated, ground and dried in vacuo at room temperature.

Polymer Characterization: $\eta$inh in $CHCl_3$ = 0.82. DSC (20° C./min): $T_m$ = 85° C.

Polymer Melt Spinning: The polymer was spun at 125° C. using an Instron Rheometer with a 40 mil die. The fiber was quenched in ice water, wound, dried in vacuo at room temperature, and subsequently drawn 5.6X at room temperature, followed by annealing at 55° C.

Fiber Properties: Diameter 8.3 mils, straight tensile strength $5.18 \times 10^4$ psi, knot tensile strength $3.51 \times 10^4$ psi, modulus $2.11 \times 10^5$ and elongation 50%.

In Vivo Evaluation: Sterilized (by $\gamma$-radiation, 2.5 Mrads), drawn fibers (9.8 mil diameter; $3.64 \times 10^4$ psi straight tensile strength; $2.34 \times 10^4$ psi knot tensile strength; $1.47 \times 10^5$ psi modulus; and an elongation of 45%) were implanted into the gluteal msucles of rats to determine their absorption and tissue response characteristics at 5, 21, 42 and 150 days post implantation.

At the 42 day period, there was no evidence of any morphologic changes of the implant sites indicating absorption. At the 150 day period, the fibers had a median value of 2 percent suture cross sectional area remaining (with a range of 0 to 20 percent).

Foreign body tissue responses to the samples were in the slight range at 5, 21 and 42 day periods and in the minimal range at the 150 day period.

In Vitro Evaluation: Drawn fibers possessing physical properties similar to those of fibers used in the in vivo testing exhibiting a 100% decrease in their initial mass after 141 days of immersion in phosphate buffer at 37° C.

EXAMPLE IX

5/95 Poly (trans 1,4-cyclohexylenedicarbonyl-cohexamethylene Oxalate)

Distilled diethyl oxalate (19.0 g, 0.130 mol), recrystallized trans 1,4-cyclohexanedimethanol (1.0 g, 0.0069 mol), 1,6-hexanediol (16.3 g, 0.138 mol), and stannous octoate (0.33 M in toluene; 0.08 ml, 0.026 mmol) were added under dry and oxygen-free conditions to a glass reactor equipped for magnetic stirring. The prepolymer was formed by heating the mixture at 120° C. for 3 hours under nitrogen at one atmosphere while allowing the formed ethanol to distill, followed by 160° C. for 2 hours. The prepolymer was heated and maintained at 205° C. for 8 hours in vacuo (0.05 mm Hg). The polymer was then cooled, isolated, ground, and dried at room temperature.

Polymer Characterization: $\eta$inh in $CHCl_3$=0.88. DSC (20° C./min): $T_m$=69° C. TGA (20° C./min. under $N_2$): Less than 0.5% weight loss at 275° C. was recorded.

Polymer Melt Spinning: The polymer was spun in an Instron Rheometer using 30 mil die at 85° C. The fibers were quenched in ice water and subsequently drawn 5X at room temperature.

Fiber Properties: Diameter=14.7 mils, straight tensile strength=$1.36 \times 10^4$ psi, knot tensile strength=$1.41 \times 10^4$ psi, modulus=$4.8 \times 10^4$ psi, elongation=90%.

In Vitro Evaluation: The drawn fibers exhibited a 93 percent decrease in their initial mass after immersion in phosphate buffer at 37° C. for 42 days.

EXAMPLE X

58/42 Poly (1,4-phenylenedicarbinyl-co-hexamethylene Oxalate)

Diethyl oxalate (14.6 g, 0.100 mols), recrystallized 1,4-benzenedimethanol (6.9 g, 0.050 mols), 1,6-hexanediol (8.3 g, 0.070 mols), and Tyzor TOT: catalyst (0.4 ml of a 1% solution) were added under dry and oxygen-free conditions to a glass reactor equipped for stirring. The prepolymer was formed by heating under nitrogen at one atmosphere at 140° C. for 4 hours while allowing the formed ethanol to distill. The mixture was then heated in vacuo (0.1 mm Hg) at 165° C. for 22 hours while continuing to remove distillates. A postpolymerization was conducted at 180, 190, and 200° C. for 2, 1 and 4 hours respectively. The polymer was cooled, ground and dried.
*Tyzor TOT, a tetraalkyl titanate catalyst manufactured by E. I. DuPont de Nemours and Co., Wilmington, Del. 19898.

Polymer Characterization: $\eta$inh in HFIP=0.48. DSC (10° C./min): $T_m$=170° C. TGA (10° C./min in $N_2$): Less than 1% cummulative weight loss experienced at 250° C.

Polymer Melt Spinning: The polymer was spun at 166° C. using an Instron Rheometer equipped with a 30 mil die.

In Vitro Evaluation: Immersion of a molded disc, 2.2 1 cm in diameter, for 8 and 78 days in phosphate buffer at 37° C. resulted in a loss of 3 and 99 percent of the initial mass, respectively.

EXAMPLE XI

56/44 Poly (1,4-phenylenedicarbinyl-co-hexamethylene Oxalate)

Dibutyl oxalate (20.2 g, 0.100 mols), 1,4-benzenedimethanol (8.3 g, 0.060 mols), 1,6-hexanediol (5.6 g, 0.047 mols), and tetraisopropylorthotitanate catalyst (0.3 ml, of a 0.01 M solution) were added under dry and oxygen-free conditions to a glass reactor equipped for magnetic stirring. The prepolymer was formed by heating at 140, and 160° C. for 1, and 17 hours respectively under nitrogen at one atmosphere while allowing the formed butanol to distill. The pressure was reduced (0.2 mm Hg) while continuing to heat at 160° C. for an additional hour. The postpolymerization of the polymer melt was completed by heating at 180° C. and 200° C. for 2, and 3.5 hours, respectively, while continuing to remove distillates. The polymer was cooled, and isolated, Polymer Characterization: $\eta$inh in HFIP=0.42. DSC (10° C./min): $T_m$=165° C. TGA (10° C./min in $N_2$): Less than 1% cummulative weight loss experienced at 250° C.

In Vitro Evaluation: Immersion of a molded disc, 2.2 cm in diameter, for 7 and 77 days, in phosphate buffer at 37° C. resulted in a loss of 3 and 56 percent of the initial mass, respectively.

EXAMPLE XII

50/50 Poly (1,4-phenylenedicarbinyl-co-hexamethylene Oxalate)

In a manner similar to that employed in Examples X and XI, the above identified copolymer having the following characteristics was produced:

DSC (10° C./min): $T_m$=175° C.

TGA (10° C./min, in $N_2$): Less than 1% cummulative weight loss experienced at 250° C.

In Vitro Evaluation: Immersion of a molded disc, 2.2 cm in diameter, for 8 and 78 days in phosphate buffer at 37° C. resulted in a loss of 6 and 54 percent of the initial mass, respectively.

While the preceding examples have been directed to the preparation of specific copolymers of polyoxalates, these examples are for purposes of illustration only and are not limiting of the invention.

Many different embodiments of this invention will be apparent to those skilled in the art and may be made without departing from the spirit and scope thereof. It is accordingly understood that this invention is not limited to the specific embodiments thereof except as defined in the appended claims.

We claim:

1. Isomorphic polyoxalate polymers consisting essentially of units of cyclic and linear oxalates and having the general formula

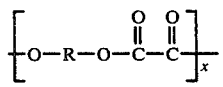

wherein each R is

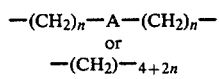

and from about 5 to 95 mol percent of the R units are I; A is trans 1,4-cyclohexylene or p-phenylene, n is 1 or 2 and is the same for I and II, and x is the degree of polymerization resulting in a polymer having an inherent viscosity of at least 0.3 as determined on a 1 gm per liter solution of polymer in chloroform or hexafluoro-isopropanol at 25° C.

2. The polymer of claim 1 wherein n is 1 and A is trans 1,4-cyclohexylene.

3. The polymer of claim 1 wherein n is 2 and A is trans 1,4-cyclohexylene.

4. The polymer of claim 1 wherein from 40 to 75 mol percent of the R groups are comprised of units of formula I.

5. The polymer of claim 1 wherein n is 1 and A is p-phenylene.

6. The polymer of claim 1 wherein n is 2 and A is p-phenylene.

7. A polymer of claim 1 having an inherent viscosity of at least about 0.5.

8. A polymer of claim 1 which is fiber forming.

* * * * *